United States Patent
Addington et al.

[11] Patent Number: 5,678,563
[45] Date of Patent: Oct. 21, 1997

[54] ASPIRATION SCREENING PROCESS FOR ASSESSING NEED FOR MODIFIED BARIUM SWALLOW STUDY

[76] Inventors: W. Robert Addington, 118 Tradewinds Ter., Indialantic; Stuart P. Miller, 705 Atlantic St., Melbourne Beach, both of Fla. 32903; Robin R. Ockey, 8603 Boutry Heights, San Antonio, Tex. 78250

[21] Appl. No.: 559,562

[22] Filed: Nov. 16, 1995

[51] Int. Cl.[6] ........................................ A61B 5/08
[52] U.S. Cl. ........................................ 128/716; 128/898
[58] Field of Search ........................ 128/716, 720, 128/204.21, 204.22, 204.23, 203.12, 773, 780, 898, 630

[56] References Cited

U.S. PATENT DOCUMENTS

| | | | |
|---|---|---|---|
| 4,558,710 | 12/1985 | Eichler | 128/720 |
| 5,024,240 | 6/1991 | McConnel | 128/780 |
| 5,143,087 | 9/1992 | Yarkony | 128/780 |

OTHER PUBLICATIONS

Horner et al., "Silent aspiration following stroke," Neurology, vol. 38, pp. 317–319 Feb. 1988.

DePippo et al., "Validation of the 3–oz Water Swallow Test for Aspiration Following Stroke," Archives of Neurology, vol. 49, pp. 1259–1261 Dec. 1992.

*Primary Examiner*—Angela D. Sykes
*Assistant Examiner*—Eric F. Winakur
*Attorney, Agent, or Firm*—Charles E. Wands

[57] ABSTRACT

Whether a (stroke) patient is at risk for oral or pharyngeal dysphagia is determined by conducting a cough-based screening process for clinically evaluating the patient's swallow. The cough-based screening methodology is able to identify those patients who require a modified barium swallow test in order to rule out aspiration, and which patients do not need a modified barium swallow test. In accordance with the process the patient attempts to cough voluntarily. If the patient is unable to cough voluntarily, the patient is required to inhale an aerosol that stimulates a sensory innervation of the patient's larynx, thereby causing the patient to cough. The resulting cough is graded to determine whether the patient is at risk to a prescribed physiological condition, in particular pneumonia. The cough tests are supplemented by monitoring the ability of the patient to hold water in the patient's mouth for a prescribed period of time. If the patient is able to hold a prescribed volume of water in the patient's mouth for the prescribed period of time, the patient need not be given a modified barium swallow test. If the patient is unable to hold a prescribed volume of water in the patient's mouth for the prescribed period of time, the patient is given a modified barium swallow test.

22 Claims, 7 Drawing Sheets

| ID# | VOLUNTARY COUGH | ASPIRATION INHALATION TEST COUGH | WATER TEST |
|---|---|---|---|
| 1 | + | − | + |
| 6 | + | + | + |
| 8 | + | − | + |
| 9 | + | + | + |
| 21 | + | − | + |
| 24 | + | + | + |

| | | WATER TEST | | | | | | | | RESPIRATORY TEST | | |
|---|---|---|---|---|---|---|---|---|---|---|---|---|
| | | H2O 15ML | | | | H2O 30ML | | | | COUGH REFLEX | | |
| MR# | MBS | GVN | RTRN | OUT MOUTH | DWN THRT | GVN | RTRN | OUT MOUTH | DWN THRT | %CON TART | VOL COUGH | INH COUGH |
| 1 | ASP | 15 | 14 | 1 | 0 | 30 | 30 | 0 | 0 | 20 | ABSENT | NORM |
| 2 | NO ASP | 7.5 | 7.5 | 0 | 0 | 25 | 25 | 0 | 0 | 20 | WEAK | NORM |
| 3 | NO ASP | 15 | 15 | 0 | 0 | 30 | 29 | 0 | 1 | 20 | NORM | NORM |
| 4 | NO ASP | 15 | 15 | 0 | 0 | 30 | 30 | 0 | 0 | 20 | WEAK | WEAK |
| 5 | PEN | 15 | 0 | 0 | 15 | 30 | 20 | 0 | 10 | 20 | NORM | NORM |
| 6 | ASP | 15 | 15 | 0 | 0 | 30 | 25 | 0 | 5 | 20 | WEAK | WEAK |
| 7 | NO ASP | 15 | 10 | 0 | 5 | 30 | 0 | 0 | 30 | 20 | WEAK | NORM |
| 8 | ASP | 15 | 14 | 0 | 1 | 30 | 30 | 0 | 0 | 20 | WEAK | NORM |
| 9 | ASP | 15 | 15 | 0 | 0 | 30 | 29 | 0 | 1 | 20 | ABSENT | WEAK |
| 10 | NO ASP | 15 | 15 | 0 | 0 | 30 | 10 | 0 | 20 | 20 | NORM | NORM |
| 11 | PEN | 15 | 14 | 1 | 0 | 30 | 20 | 0 | 10 | 20 | NORM | NORM |
| 12 | NO ASP | 15 | 15 | 0 | 0 | 30 | 30 | 0 | 0 | 20 | NORM | NORM |
| 13 | NO ASP | 15 | 10 | 5 | 0 | 30 | 25 | 5 | 0 | 20 | NORM | NORM |
| 14 | PEN | 15 | 15 | 0 | 0 | 30 | 30 | 0 | 0 | 20 | NORM | NORM |
| 15 | NO ASP | 15 | 14 | 1 | 0 | 30 | 15 | 0 | 15 | 20 | WEAK | WEAK |
| 16 | PEN | 15 | 9 | 0 | 6 | 30 | 4 | 0 | 26 | 20/50 | WEAK | WEAK |
| 17 | PEN | 15 | 0 | 0 | 15 | 30 | 0 | 0 | 30 | 20 | WEAK | NORM |
| 18 | NO ASP | 15 | 10 | 0 | 5 | 30 | 10 | 0 | 20 | 20 | WEAK | NORM |
| 19 | PEN | 15 | 1 | 5 | 9 | 30 | 15 | 5 | 10 | 20 | WEAK | NORM |
| 20 | NO ASP | 15 | 0 | 1 | 14 | PT UNABLE TO TOLERATE TEST | | | | 20 | NORM | NORM |
| 21 | ASP | 15 | 14 | 1 | 0 | 30 | 25 | 5 | 0 | 20 | WEAK | NORM |
| 22 | NO ASP | 15 | 14 | 1 | 0 | 30 | 25 | 5 | 0 | 20 | WEAK | WEAK |
| 23 | PEN | 15 | 15 | 0 | 0 | 30 | 30 | 0 | 0 | 20 | WEAK | NORM |
| 24 | ASP | 15 | 10 | 5 | 0 | 30 | 0 | 30 | 0 | 20 | WEAK | WEAK |
| 25 | NO ASP | 15 | 15 | 0 | 0 | 30 | 29 | 1 | 0 | 20 | NORM | NORM |
| 26 | NO ASP | 15 | 15 | 0 | 0 | 30 | 30 | 0 | 0 | 20 | NORM | NORM |
| 27 | NO ASP | 15 | 15 | 0 | 0 | 30 | 30 | 0 | 0 | 20 | NORM | NORM |
| 28 | PEN | 15 | 10 | 0 | 5 | 30 | 0 | 0 | 30 | 20 | WEAK | NORM |
| 29 | NO ASP | 15 | 15 | 0 | 0 | 25 | 25 | 0 | 0 | 20 | NORM | NORM |
| 30 | NO ASP | 15 | 15 | 0 | 0 | 30 | 29 | 1 | 0 | 20/50 | WEAK | WEAK |
| 31 | NO ASP | 15 | 15 | 0 | 0 | 30 | 30 | 0 | 0 | 20 | WEAK | WEAK |
| 32 | PEN | 15 | 15 | 0 | 0 | 30 | 20 | 0 | 10 | 20/50/80 | ABSENT | ABSENT |
| 33 | PEN | 15 | 15 | 0 | 0 | 30 | 30 | 0 | 0 | 20 | WEAK | NORM |
| 34 | PEN | 15 | 10 | 0 | 5 | 30 | 20 | 5 | 5 | 20 | WEAK | NORM |
| 35 | NO ASP | 15 | 10 | 0 | 5 | 30 | 24 | 0 | 6 | 20 | ABSENT | NORM |
| 36 | NO ASP | 15 | 14 | 0 | 1 | 30 | 29 | 0 | 1 | 20 | NORM | NORM |
| 37 | NO ASP | 14 | 13 | 0 | 1 | 30 | 30 | 0 | 0 | 20 | NORM | NORM |
| 38 | NO ASP | 15 | 15 | 0 | 0 | 30 | 30 | 0 | 0 | 50 | WEAK | WEAK |
| 39 | NO ASP | 15 | 14 | 1 | 0 | 29 | 29 | 0 | 0 | 20 | NORM | NORM |
| 40 | PEN | 15 | 15 | 0 | 0 | 30 | 20 | 10 | 0 | 20 | NORM | NORM |

*FIG. 3*

|      |                  | NO ASPIRATION         |            |
|------|------------------|-----------------------|------------|
| ID#  | VOLUNTARY COUGH  | INHALATION TEST COUGH | WATER TEST |
| 2    | +                | −                     | −          |
| 3    | −                | −                     | +          |
| 4    | +                | +                     | −          |
| 7    | +                | −                     | +          |
| 10   | −                | −                     | +          |
| 12   | −                | −                     | −          |
| 13   | −                | −                     | +          |
| 15   | +                | +                     | +          |
| 18   | +                | −                     | +          |
| 20   | −                | −                     | +          |
| 22   | +                | +                     | +          |
| 25   | −                | −                     | +          |
| 26   | −                | −                     | −          |
| 27   | −                | −                     | −          |
| 29   | −                | −                     | −          |
| 30   | +                | +                     | +          |
| 31   | +                | +                     | −          |
| 35   | +                | −                     | +          |
| 36   | −                | −                     | +          |
| 37   | −                | −                     | +          |
| 38   | +                | +                     | −          |
| 39   | −                | −                     | +          |

*FIG. 5*

|      |                  | PENETRATION           |            |
|------|------------------|-----------------------|------------|
| ID#  | VOLUNTARY COUGH  | INHALATION TEST COUGH | WATER TEST |
| 5    | −                | −                     | +          |
| 11   | −                | −                     | +          |
| 14   | −                | −                     | −          |
| 16   | +                | +                     | +          |
| 17   | +                | −                     | +          |
| 19   | +                | −                     | +          |
| 23   | +                | −                     | −          |
| 28   | +                | −                     | +          |
| 32   | +                | +                     | +          |
| 33   | +                | −                     | −          |
| 34   | +                | −                     | +          |
| 40   | −                | −                     | +          |

*FIG. 6*

|  | NORMAL | ABNORMAL | TOTAL |
|---|---|---|---|
| NO ASPIRATION PENETRATION | 16 | 18 | 34 |
| ASPIRATION | 0 | 6 | 6 |
| TOTAL | 16 | 24 | 40 |

$x^2 = 4.706$, $p = 0.035$ BY FISHER EXACT TEST

*FIG. 7*

|  | PNEUMONIA | NO PNEUMONIA | TOTAL |
|---|---|---|---|
| NORMAL | 0 | 29 | 29 |
| ABNORMAL | 3 | 8 | 11 |
| TOTAL | 3 | 37 | 40 |

$x^2 = 8.55$, $p = 0.017$ BY FISHER EXACT TEST

*FIG. 8*

|  | ASPIRATION | NO ASPIRATION | TOTAL |
|---|---|---|---|
| UNABLE TO PERFORM | 4 | 3 | 7 |
| ABLE TO PERFORM | 6 | 34 | 40 |
| TOTAL | 10 | 37 | 47 |

$x^2 = 6.317$, $p = 0.029$ BY FISHER EXACT TEST

*FIG. 9*

| FACTOR | LOGISTIC COEFFICIENT | STANDARD ERROR (SE) | COEFF/SE | P |
|---|---|---|---|---|
| VOLUNTARY | −3.88 | 1.91 | −2.04 | 0.05 |
| CONSTANT | 4.98 | 1.85 | 2.69 | |

| VOLUNTARY COUGH | WATER TEST | PREDICTED PROBABILITY OF NO ASPIRATION |
|---|---|---|
| + | − | 0.99 |
| − | + | 0.99 |
| − | − | 1.00 |
| + | + | 0.67 |

FIG. 10

| | MBS + ASP | MBS − ASP |
|---|---|---|
| VOL COUGH + | 6 | 18 |
| VOL COUGH − | 0 | 16 |

- SENS 6/6 = 100%
- SPEC 16/34 = 47.06%
- PVNT 0/16 = 0%
- PVPT 6/24 = 25%

FIG. 11

|  | GOLD STAND + | GOLD STAND − |
|---|---|---|
| POSITIVE TEST | a=TRUE | b=FALSE |
| NEGATIVE TEST | c=FALSE | d=TRUE |

- SENS − a/a+c
- SPEC − d/b+d
- PVNT − c/c+d
- PVPT − a/a+b

*FIG. 12*

|  | MBS + ASP | MBS − ASP |
|---|---|---|
| VOL COUGH / H$_2$O + | 6 | 12 |
| EITHER OR BOTH nl | 0 | 22 |

- SENS 6/6 = 100%
- SPEC 22/34 = 64.70%
- PVNT 0/22 = 0%
- PVPT 6/18 = 33.33%

*FIG. 13*

ASPIRATION SCREENING PROCESS FOR ASSESSING NEED FOR MODIFIED BARIUM SWALLOW STUDY

FIELD OF THE INVENTION

The present invention relates in general to the field of speech pathology, and is particularly directed to a process for determining whether a patient is at risk for oral or pharyngeal dysphagia, by means of a cough-based screening process for clinically evaluating the patient's swallow.

BACKGROUND OF THE INVENTION

In order to clinically detect those patients who are at risk for aspiration, speech pathologists currently employ a standard procedure for evaluating a patient's swallow. A normal human swallow can be separated into four phases: 1)—oral preparation, 2)—the oral phase, 3)—the pharyngeal phase, and 4)—the esophageal phase. Patients who have suffered a stroke, traumatic brain injury or neuromuscular disorder (such as MS or ALS) have an increased risk of aspiration, and may have difficulty with either the oral phase, the pharyngeal phase or both, secondary to neurologic deficits. Poor tongue movement in chewing or in the swallow can cause food to fall into the pharynx and into the open airway before the completion of the oral phase. A delay in triggering the pharyngeal swallowing reflex can result in food falling into the airway during the delay when the airway is open. Reduced peristalsis in the pharynx, whether unilateral or bilateral, will cause residue in the pharynx after the swallow that can fall or be inhaled into the airway. Laryngeal or cricopharyngeal dysfunction can lead to aspiration because of decreased airway protection during the swallow.

An abnormal human swallow is termed dysphagia. The oropharyngeal physiology involved in a normal swallow is very complicated, and many different neurological disturbances can disrupt normal swallowing and can cause aspiration of food material, liquid or solid, into the lungs, leading to increased morbidity in hospitalized patients and possible pneumonia. See, for example, the article by Jeri Logemann, entitled: "Swallowing Physiology and Pathophysiology," Otolaryngologic Clinics of North America, Vol. 21, No. 4, November 1988, and the article by L. Kaha et. al., entitled: "Medical Complications During Stroke Rehabilitation, Stroke Vol. 26, No. 6, June 1995.

Speech pathologists have tried many procedures to detect or predict aspiration in patients with neurological deficits. Although the standard bedside swallow exam to screen patients is beneficial for evaluating patients at risk for oral or pharyngeal dysphagia, studies have shown that, when compared to a modified barium swallow (MBS) videofluoroscopic examination, it is neither very specific nor sensitive in detecting aspiration. See, for example, the article by Mark Splaingard et. al. entitled: "Aspiration in Rehabilitation Patients: Videofluoroscopy vs. Bedside Clinical Assessment; Archives of Physical Medicine and Rehabilitation, Vol. 69, August 1988, and the article by P. Linden, et. al., entitled" "The Probability of Correctly Predicting Subglottic Penetration from Clinical Observations", Dysphagia, 8: pp 170–179, 1993.

As discussed in the above-referenced Logemann article, and also in an article entitled: "Aspiration of High-Density Barium Contrast Medium Causing Acute Pulmonary Inflammation—Report of Two Fatal Cases in Elderly Women with Disordered Swallowing," by C, Gray et al, Clinical Radiology, Vol. 40, 397–400, 1989, videofluoroscopic evaluations are more costly than bedside evaluations and videofluoroscopy is not entirely without risk. Because of the poor predictability of the present bedside exams, the MBS is being used more and more with its increased reliability for diagnosing aspiration. Many studies using videofluoroscopy have tried to pinpoint the exact anatomical or neurological deficit causing the dysphagia, as well as what stage of the swallow is primarily affected in different disorders.

Patients that have a head injury, stroke or other neuromuscular disorder can aspirate before, during, or after the swallow, and a high percentage can be silent aspirators. Unfortunately, these patients might not display any indication of aspiration during a clinical exam but can be detected by the MBS, as discussed in the Logemann article and in an article by C. Lazurus et al, entitled: "Swallowing Disorder in Closed Head Trauma Patients," Archives of Physical Medicine and Rehabilitation, Vol. 68, February 1987, an article by J. Logemann, entitled: "Effects of Aging on the Swallowing Mechanism," Otolaryngologic Clinics of North America, Vol. 23, No. 6, December 1990, and an article by M. DeVito et. al., entitled: "Swallowing Disorders in Patients with Prolonged Orotracheal Intubation or Tracheostomy Tubes," Critical Care Medicine, Vol. 18, No. 12, 1990.

The bedside swallow exam performed by most speech pathologists evaluates history, respiratory status, level of responsiveness and an oral exam. The oral examination includes a detailed evaluation of the muscles of mastication, lips, tongue, palate, position patient tested in as well as the swallowing evaluation. Sensation, various movements and strength are carefully evaluated. In the pharyngeal stage, the patient is tested for a dry swallow, thin liquid, thick liquid, pureed textures and solid textures.

A typical bedside exam looks for nasal regurgitation, discomfort or obstruction in the throat or multiple swallows, as well as any visible signs that may indicate risk for aspiration, gurgling, impaired vocal quality, and coughing. The bedside exam results are then analyzed to determine whether the patient should have an MBS study to evaluate swallowing physiology and to rule out aspiration. Although the bedside exam is very thorough, and can identify patients who are at risk for or have dysphagia, it is not effective in determining which patients will aspirate.

In addition to the foregoing, speech pathologists have historically had difficulty studying the sensory afferents of the larynx involved in airway protection. As described in an article by J. Widdicombe et al, entitled: "Upper Airway Reflex Control," Annual New York Academy of Science, Vol. 533, 252–261, 1988, the sensory afferents for general coughing travel the internal branch of the superior laryngeal nerve. A patient may have a voluntary cough present with the efferent motor system intact, but not have any sensation on the larynx secondary to the afferents becoming completely or partially affected, which would be indicative of risk for silent aspiration.

As described above, the MBS test is of value to patients that silently aspirate. The difficulty arises in deciding which patients should have an MBS test. Not all patients with a closed head injury or a stroke will aspirate. Further, it is not economically realistic to evaluate all patients with neurologic deficits for aspiration using an MBS test. It would be beneficial therefore to have a method to clinically screen patients with neurologic deficits that have dysphagia, and to more accurately predict which patients are at risk of aspiration and which patients are not.

SUMMARY OF THE INVENTION

In accordance with the present invention, the shortcomings of the above-described conventional processes employed by speech pathologists to detect aspiration in patients with neurological deficits are effectively remedied by a cough-based screening process which is operative to clinically detect a (stroke) patient who is at risk for aspiration in both oral and pharyngeal phases of the human swallow. The inventive screening methodology is able to identify those patients who require an MBS test in order to rule out aspiration, and which patients do not need an MBS.

The initial step according to the cough-based screening process of present invention involves a pharyngeal test, in which the patient is given two separate tasks to perform. The patient will have been diagnosed as having had a stroke, and is potentially scheduled to undergo a modified barium swallow (MBS) test. The patient should not be one with a history of asthma or on supplemental oxygen for dyspnea. A speech pathologist performs a preliminary general bedside swallow evaluation and also tests for cognition, voice quality and cranial nerves.

In the first step of the pharyngeal test the patient is required to voluntarily cough. The patient's ability to voluntarily cough is a reflection of the function of the patient's efferent motor system, and is graded by the testing pathological specialist as either normal or decreased, if the patient is able to successfully cough. The patient may then optionally be administered a water-holding test, in which the patient is asked to hold a given amount of water in the patient's mouth for a given period of time.

If the patient is not able to cough voluntarily, the patient is subjected to an inhalation cough test, in which a sensory innervation to the patient's larynx is tested. As will be described, this sensory innervation test of the patient's larynx is carried out by stimulating nociceptor (irritant) and C-fibre receptors, using an aerosol chemostimulant that is inhaled through the patient's mouth.

In accordance with a preferred embodiment of the present invention, the aerosol inhalant, which may be delivered by a standard aerosol inhaler, comprises an atomized solution of tartrate mixed with saline. Although other receptor specific chemostimulants may be employed, studies involving inhaling tartrate, reveal that tartrate will stimulate a cough 100% of the time in normal individuals. Further, tartrate is considered safe, does not cause pain or discomfort, and has not been shown to cause bronchoconstriction or complications in asthmatics when inhaled in an aerosol form.

During the inhalation cough test, the aerosol stimulant is injected into the patient's mouth by a respiratory therapist, using a nebulizer for a relatively brief period of time. The patient is tested a maximum of three times at different stimulant strengths until a cough is elicited. During each successive stimulant application, the patient receives progressively increasing concentrations of the aerosol for the prescribed period of time by tidal breathing at one minute intervals using successively increasing percentage concentrations.

In response to the patient coughing as a result of the inhaled aerosol stimulant, the inhalation cough test is terminated, regardless of the percentage of concentrations used. The patient's response to the inhalation test is graded as either a low pneumonia risk (if the patient coughs immediately in response to the initial aerosol spray and the cough appears strong or normal) or a high pneumonia risk (where the cough appears weak or the patient does not readily cough in response to the initial concentration spray, but requires a more concentrated aerosol application).

Upon completion of the inhalation cough test, the water holding test is conducted. During the water-holding test, the patient is required to take two separate volumes of water into the mouth and hold the water for a specified period of time. Two separate volumes of water are used, since aspiration can occur with large volumes or smaller volumes separately. During the water holding test, the patient is instructed not to swallow any of the water and, at the end of the specified time, to return the held water to a measuring receptacle. Any water that is lost out of the patient's mouth as a result of a facial droop or poor labial control is collected and measured. Also, the total water returned to the measuring receptacle is calculated, in order to determine if water may have spilled over into the pharynx should there be any of the original volume of water not recollected.

BRIEF DESCRIPTION OF THE DRAWINGS

FIG. 2 diagrammatically illustrates the use of an aerosol inhaler in the inhalation cough phase of the process of the present invention;

FIGS. 3-6 diagrammatically tabulate the results of conducting the screening process of the present invention for individual ones of a group of stroke patients;

FIG. 7 tabulates the results of the voluntary cough test of the present invention for forty stroke patients into normal and abnormal coughs, classified as no aspiration and penetration combined together versus an aspiration group;

FIG. 8 tabulates the results of the inhalation cough test of the present invention for forty stroke patients showing those diagnosed as developing pneumonia and no pneumonia, classified as normal and abnormal groups;

FIG. 9 tabulates the classification of MBS for two groups of stroke patients including forty patients who were able to perform and an additional seven patients who were not able to perform the tests, in terms of aspiration and no aspiration;

FIG. 10 tabulates multivariate association by stepwise logistic regression for no aspiration diagnosis;

FIG. 11 provides a matrix relationship between MBS aspiration (+) and (-) and a voluntary cough (+) and (-);

FIG. 12 tabulates Gold Standard ratio definitions; and

FIG. 13 provides a matrix relationship between MBS aspiration (+) and (-) and a voluntary cough/water test combinted (+) and either or both nl.

DETAILED DESCRIPTION

As described briefly above, the steps of the cough-based screening process of the present invention are operative to clinically detect a (stroke) patient, who is at risk for aspiration (one of the characteristics of dysphagia), by evaluating the patient for both oral and pharyngeal phases of the human swallow. The inventive screening methodology is able to identify those patients who require an MBS test in order to rule out aspiration, and which patients do not need an MBS for that purpose. In addition, the invention quantifies the risk of aspiration based on the results of the bedside screen test compared to the MBS test.

Figure 1:
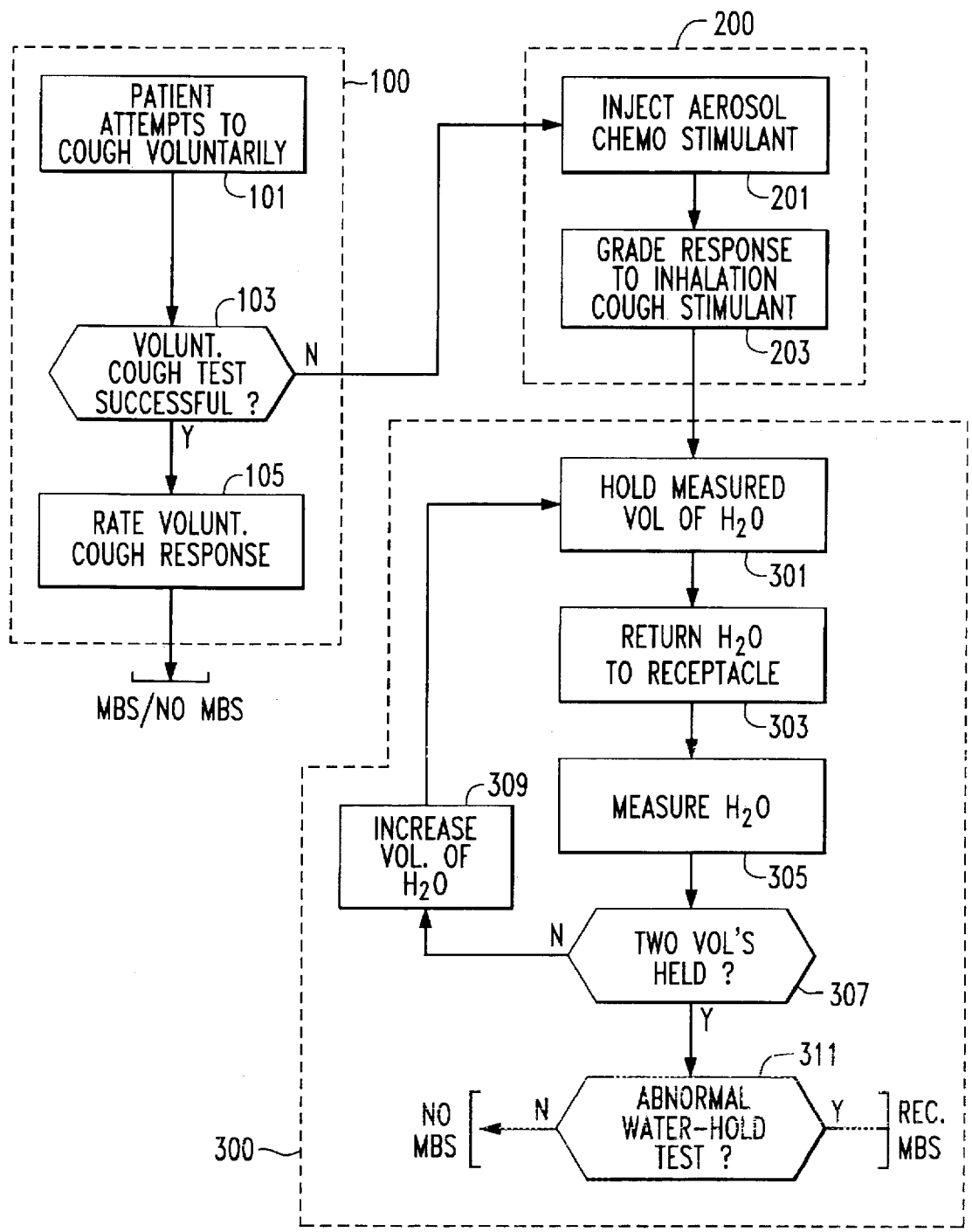
FIG. 1 is a flow diagram of the cough-based screening process for determining whether a patient is at risk for oral or pharyngeal dysphagia in accordance with the present invention.

Referring now to the flow diagram of FIG. 1, the cough-based screening process according to the present invention begins with a pharyngeal test, shown at 100, in which the patient is given two separate physiologic tasks to perform. Typically, the patient will be an adult individual, who has been diagnosed as having had a stroke, has already been scheduled to undergo a (not yet administered) modified barium swallow (MBS) test, and is able to follow commands and give informed consent to participate. The patient should not be one with a history of asthma or on supplemental oxygen for dyspnea. A speech pathologist performs a preliminary general bedside swallow evaluation and also tests for cognition, voice quality and cranial nerves.

The first step in the pharyngeal test 100 (STEP 101) is to ask the patient to voluntarily cough. The patient's ability to voluntarily cough is a reflection of the function of the patient's efferent motor system, and is characterized or scored by the testing pathological specialist as either normal, decreased or absent. If the patient is able to successfully cough (the answer to query STEP 103 is YES), the patient's response is rated in step 105 as either normal or decreased, depending upon the testing pathologist's estimation of the cough response. The patient may then optionally be administered a water-holding test, shown at 300 and to be described, in which the patient is asked to hold a given amount of water in the patient's mouth for a given period of time.

If the patient does not pass the voluntary cough test, namely, is not able to cough voluntarily or the cough is decreased (the answer to query STEP 103 is NO), the voluntary cough is rated as absent or decreased, and the patient is then subjected to an inhalation cough test 200, in which a sensory innervation to the patient's larynx is tested. As noted briefly above, this sensory innervation test of the patient's larynx is carried out by stimulating nociceptor (irritant) and C-fibre receptors, using an aerosol chemostimulant that is inhaled through the patient's mouth. As diagrammatically illustrated in FIG. 2, during the inhalation cough test, the patient wears a noseclip 20.

There is increasing evidence that reflexes for cough and bronchoconstriction are mediated by different pathways, and there are numerous chemostimulants which are receptor specific. See, for example, the article entitled "Regional Sensitivity of the Respiratory Tract to Stimuli Causing Cough and Reflex Bronchoconstriction," by J. Karlson et. al, Respiratory Medicine, 85 (Supplement A): 47–50, 1991, the text "Cough Receptor Sensitivity and Bronchial Responsiveness in Normal and Asthmatic Subjects," European Respiratory Journal, 56: 291–295, 1992, and the article entitled: "Effects of Methacholine Induced Bronchoconstriction and Procaterol-Induced Bronchodilation on Cough Receptor Sensitivity to Inhaled Capsaicin and Tartaric Acid," by M. Fujimura al., Thorax, 47: pp 441–445, 1992.

Figures 2, 4:
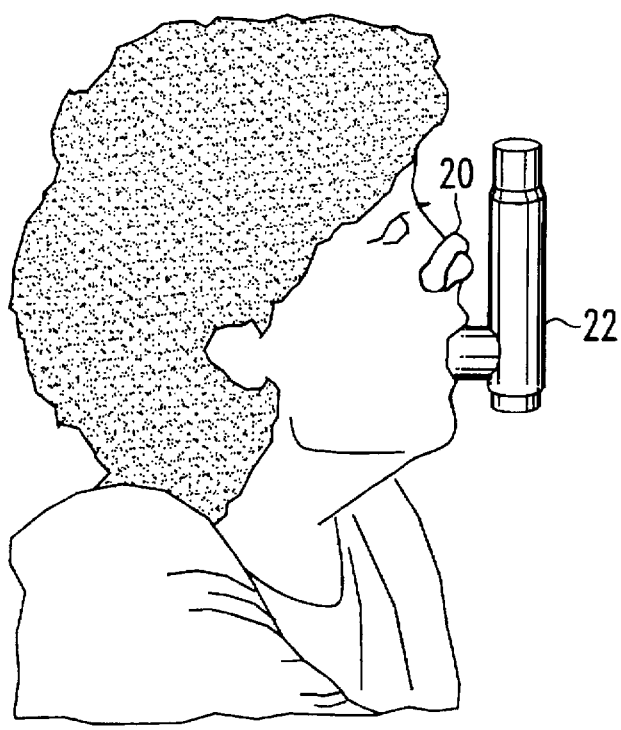

In accordance with a preferred embodiment of the present invention, the aerosol inhalant, which may be delivered by a standard aerosol inhaler, such as a commerically available Bennett Twin nebulizer, shown at 22 in FIG. 2, comprises an atomized solution of tartrate mixed with saline. Although other receptor specific chemostimulants may be employed, studies involving inhaling tartrate, as described in the article entitled: "Cough Receptor Sensitivity and Bronchial Responsiveness in Normal and Asthmatic Subjects," by M. Fujimura et al, European Respiratory Journal, 56: 291–295, 1992, in the text entitled: "Clinical Toxicology of Commercial Products, Tartaric Acid," Fifth Ed., p 563, Williams and Wilkins, Baltimore/London, in the reference text entitled: "Martindale: The Extra Pharmacopoedia," Twenty Ninth Edition, The Pharmaceutical Press, London, 1989, and in the above-referenced Linden article have revealed that tartrate will stimulate a cough 100% of the time in normal individuals.

Moreover, tartrate is considered safe, does not cause pain or discomfort, and has not been shown to cause bronchoconstriction or complications in asthmatics when inhaled in an aerosol form. See, for example, the article by M. Fujimura et al, entitled: "Sex Difference in the Inhaled Tartaric Acid Cough Threshold in Non-Atopic Healthy Subjects," Thorax, 45:633–634, and the previously referenced articles by M. Fujimura et al, and the Williams and Wilkins, and Martindale texts.

During the first step (STEP 201) of the inhalation cough test 200, the aerosol chemostimulant is injected into the patient's mouth by a respiratory therapist, using nebulizer 22 for a prescribed period of time (e.g., on the order of 15 seconds). The nebulizer output spray rate may be on the order of 0.2 ml/min. as a non-limiting example. During STEP 201, the patient is tested a maximum of three times at different stimulant strengths until a cough is elicited. During each successive chemostimulant application, the patient receives progressively increasing concentrations of the aerosol for the prescribed period of time by tidal breathing at one minute intervals using successively increasing percentage concentrations (e.g. 20, 50 and 80 percent).

Once the patient elicits a cough as a result of the inhaled aerosol stimulant in STEP 201, the inhalation cough test is terminated, regardless of the percentage of concentrations used. Next, the patient's response to the inhalation test is graded in STEP 203 as either a low pneumonia risk (as in the case where the patient coughs immediately in response to the initial aerosol spray) or a high pneoumonia risk (in the case where a cough is present but decreased, or the patient does not readily cough in response to the initial concentration spray, but requires a more concentrated aerosol application).

Upon completion of the inhalation cough test 200, the water holding test 300 is conducted. As noted earlier, the water-holding test may also be carried out after or in parallel with the voluntary cough test 100, described above. In the water-holding test, the patient is required to take two separate volumes of water into the mouth and hold the water for a specified period of time (e.g. on the order of ten seconds). Two separate volumes of water are used, since aspiration can occur with large volumes or smaller volumes separately, as described in the previously referenced Logemann article.

During STEP 301 of the water holding test 300, the patient is instructed not to swallow any of the water and, at the end of the specified time (STEP 303) to return it to a measuring receptacle. The first volume of water given to the patient may be on the order of 15 ml, as a non-limiting example. Any water that is lost out of the patient's mouth as a result of a facial droop or poor labial control is collected and measured (STEP 305). In addition, the total water returned to the measuring receptacle is calculated, in order to assess what water may have spilled over into the pharynx if any of the volume is missing. In query STEP 307, a determination is made whether the water holding test has been conducted for two separate volumes of water. If the answer to query STEP 307 is NO, a second vial of water is given to the patient in step 309, and the process returns to step 301. The second volume of water may be on the order of 30 ml, as a non-limiting example. If the answer to query STEP 307 is YES, the process proceeds to query STEP 311.

In query STEP 311, based upon the results of STEP 305, a determination is made as to whether the patient has passed the water-holding test, namely—no water has been lost out of the patient's mouth and no water has spilled over into the patient's pharynx. If the answer to query STEP 311 is NO, it is concluded that the patient need not be given an MBS test. (In a test evaluation of performing the water test-holding test steps on twenty normal individuals, ages 30–72, for both volumes, no changes in volume return (p<0.01) were measured in STEP 305.) If, however, the answer to query STEP 311 is YES (there has been spillage or leakage from the patient's mouth), then it is concluded that the patient should be given an MBS test.

EXAMPLE

FIGS. 3–12 diagrammatically tabulate the results of conducting the foregoing described methodology, using the component concentrations and volumes of tartrate saline and water described above for a group of stroke patients of the various ages listed. In the Figures, each (+) indicates that the patient failed the specified phase (voluntary cough, inhalation cough, water-holding test) of the process, while a (−) indicates that the patient passed that phase of the process.

In addition to the individual patient responses listed in FIGS. 3–6, FIG. 7 tabulates the results of the voluntary cough test for the forty stroke patients into normal and abnormal coughs, classified as no aspiration and penetration combined together versus the aspiration group.

FIG. 8 tabulates the results of the inhalation cough test for the forty patients showing those diagnosed as developing pneumonia and no pneumonia, classified as normal and abnormal groups. It may be noted that no patient who exhibited a normal cough response to this test developed pneumonia.

FIG. 9 tabulates the classification of MBS for two groups of patients including the forty patients who were able to perform and an additional seven patients who were not able to perform the tests (for a total of forty-seven patients), in terms of aspiration and no aspiration.

FIG. 10 tabulates multivariate association by stepwise logistic regression for no aspiration diagnosis. FIG. 10 reveals no predicted probablity of aspiration for any patient who passed the voluntary cough and water-holding tests.

FIG. 11 provides a matrix relationship between MBS aspiration (+) and (−) and a voluntary cough (+) and (−). Associated with the matrix of FIG. 11 are the ratios of sensitivity (SENS), specificity (SPEC), predictive value of negative test (PVNT) and predictive value of positive test (PVPT), defined in accordance with the Gold Standard ratio definitions listed in FIG. 12.

FIG. 13 provides a matrix relationship between MBS aspiration (+) and (−) and a voluntary cough/water test combinted (+) and either or both nl. Also associated with the matrix of FIG. 13 are the ratios of sensitivity (SENS), specificity (SPEC), predictive value of negative test (PVNT) and predictive value of positive test (PVPT).

As will be appreciated from the foregoing description, whether a (stroke) patient is at risk for oral or pharyngeal dysphagia is readily determined in accordance with the cough-based screening process of the present invention, which is able to identify those patients who require a modified barium swallow test in order to rule out aspiration, and which patients do not need a modified barium swallow test. By requiring a patient who is unable to cough voluntarily to inhale an aerosol that stimulates a sensory innervation of the patient's larynx, and thereby causes the patient to cough involuntarily, the patient can be graded to determine whether the patient is at risk to pneumonia. Supplementing the cough tests with the water-holding test allows a determination of whether the patient is permitted to be given a modified barium swallow test.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed:

1. A method of evaluating a patient having a potential neurological deficit to determine whether the patient is at risk for to a prescribed physiological condition, comprising the steps of:
   (a) having the patient attempt to cough voluntarily;
   (b) in response to the patient being unable to cough voluntarily, having the patient inhale an aerosol that stimulates a sensory innervation of the patient's larynx, thereby causing the patient to cough; and
   (c) evaluating the cough of the patient in step (b) to determine whether the patient is at risk to said prescribed physiological condition.

2. A method according to claim 1, further including the step of (d) having the patient hold water in the patient's mouth and monitoring the ability of the patient to hold the water in the patient's mouth for a prescribed period of time.

3. A method according to claim 2, further including the step of (e), in response to the patient being able to hold a prescribed volume of water in the patient's mouth for said prescribed period of time, identifying the patient as one who need not be given a modified barium swallow test.

4. A method according to claim 2, further including the step of (e), in response to the patient being unable to hold a prescribed volume of water in the patient's mouth for said prescribed period of time, identifying the patient as one who should be given a modified barium swallow test.

5. A method according to claim 1, wherein step (b) comprises having the patient inhale an aerosol containing a chemical that is effective to stimulate nociceptor (irritant) and C-fibre receptors in the patient's throat.

6. A method according to claim 1, wherein step (b) comprises having the patient to inhale an aerosol containing tartrate mixed with saline.

7. A method according to claim 1, wherein step (b) comprises having the patient inhale an aerosol containing respectively different stimulant strengths of a chemical that is effective to stimulate a sensory innervation of the patient's larynx.

8. A method according to claim 1, wherein step (b) comprises having the patient successively inhale an aerosol containing respectively increasing concentrations of a chemostimulant that is effective to stimulate a sensory innervation of the patient's larynx.

9. A method according to claim 8, wherein said chemostimulant is a saline solution of tartrate.

10. A method according to claim 1, wherein said prescribed physiological condition is pneumonia.

11. A method of evaluating a patient having a potential neurological deficit to determine whether the patient is at risk to a prescribed physiological condition, comprising the steps of:

(a) having the patient inhale an aerosol that stimulates a sensory innervation of the patient's larynx, thereby having the patient to cough; and (b) evaluating the cough of the patient in step (a) to determine whether the patient is at risk to said prescribed physiological condition.

12. A method according to claim 11, wherein said prescribed physiological condition is pneumonia.

13. A method according to claim 11, further including the step (c) of monitoring the ability of the patient to hold water in the patient's mouth for a prescribed period of time.

14. A method according to claim 13, further including the step of (d), in response to the patient being able to hold a prescribed volume of water in the patient's mouth for said prescribed period of time, identifying the patient as one who need not be given a modified barium swallow test.

15. A method according to claim 13, further including the step of (d), in response to the patient being unable to hold a prescribed volume of water in the patient's mouth for said prescribed period of time, identifying the patient as one who should be given a modified barium swallow test.

16. A method according to claim 11, wherein step (a) comprises having the patient inhale an aerosol containing a chemical that is effective to stimulate nociceptor (irritant) and C-fibre receptors in the patient's throat.

17. A method according to claim 11, wherein step (a) comprises having the patient inhale an aerosol containing tartrate mixed with saline.

18. A method according to claim 11, wherein step (a) comprises having the patient inhale an aerosol containing respectively different stimulant strengths of a chemical that is effective to stimulate a sensory innervation of the patient's larynx.

19. A method according to claim 11, wherein step (a) comprises having the patient successively inhale an aerosol containing respectively increasing concentrations of a chemostimulant that is effective to stimulate a sensory innervation of the patient's larynx.

20. A method according to claim 19, wherein said chemostimulant is a saline solution of tartrate.

21. A method according to claim 19, wherein, during said successive stimulant inhalations of said chemostimulant, the patient receives said respectively increasing concentrations of the aerosol by tidal breathing at prescribed time intervals.

22. A method according to claim 19, wherein step (b) comprises grading the cough of the patient as either a low pneumonia risk where the patient's cough appears normal in response to the initial aerosol spray, or a high pneumonia risk where the patient has a decreased or weak cough in response to the initial concentration spray or requires a more concentrated aerosol application to elicit a cough.

* * * * *

UNITED STATES PATENT AND TRADEMARK OFFICE
CERTIFICATE OF CORRECTION

PATENT NO. : 5,678,563

DATED : October 21, 1997

INVENTOR(S) : W. Robert Addington, Robert E. Stephens
Robin R. Ockey

It is certified that error appears in the above-identified patent and that said Letters Patent is hereby corrected as shown below:

On the title page, item [76], the names and addresses of the inventors should read:

W. Robert Addington
118 Tradewinds Terrace
Indialantic, Florida  32903

Robert E. Stephens
5224 Northwest Bluff Drive
Parkville, Missouri  64152

Robin R. Ockey
8603 Boutry Heights
San Antonio, Texas  78250

Signed and Sealed this

Seventeenth Day of March, 1998

Attest:

BRUCE LEHMAN

Attesting Officer

Commissioner of Patents and Trademarks